(12) United States Patent
Wang et al.

(10) Patent No.: US 10,898,888 B2
(45) Date of Patent: Jan. 26, 2021

(54) PREPARATION AND APPLICATION OF MAGNETIC METALLIC OXIDE CROSS-LINKED ACIDIC POLYIONIC LIQUID

(71) Applicant: Jiangnan University, Wuxi (CN)

(72) Inventors: Haijun Wang, Wuxi (CN); Chunyan Wu, Wuxi (CN); Yi Huang, Wuxi (CN); Wenwen Yuan, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/359,303

(22) Filed: Mar. 20, 2019

(65) Prior Publication Data

US 2019/0217281 A1 Jul. 18, 2019

Related U.S. Application Data

(63) Continuation of application No. PCT/CN2017/117041, filed on Dec. 18, 2017.

(30) Foreign Application Priority Data

Dec. 29, 2016 (CN) .......................... 2016 1 1242187
Dec. 29, 2016 (CN) .......................... 2016 1 1242194

(51) Int. Cl.
*B01J 31/02* (2006.01)
*B01J 37/08* (2006.01)
(Continued)

(52) U.S. Cl.
CPC ......... *B01J 31/0284* (2013.01); *B01J 23/745* (2013.01); *B01J 23/835* (2013.01);
(Continued)

(58) Field of Classification Search
CPC ........ B01J 21/04; B01J 21/063; B01J 21/066; B01J 21/08; B01J 31/0254; B01J 31/0284;
(Continued)

(56) References Cited

U.S. PATENT DOCUMENTS 9,397,366 B2 * 7/2016 Archer ................ H01M 10/052
2009/0313889 A1 * 12/2009 Zhang .................. B01J 31/2269
44/350
2011/0319695 A1 * 12/2011 Hommeltoft ............. C07C 2/60
585/724

FOREIGN PATENT DOCUMENTS

CN 103242269 A 8/2013
CN 106166499 A 11/2016
WO 2008095069 A2 8/2008

OTHER PUBLICATIONS

Govan et al., Recent Advances in the Application of Magnetic Nanoparticles as a Support for Homogeneous Catalysts, Nanomaterials 2014, 4, 222-241.*

(Continued)

*Primary Examiner* — Jun Li
(74) *Attorney, Agent, or Firm* — IPro, PLLC; Na Xu

(57) ABSTRACT

The present disclosure discloses the preparation and application of magnetic metallic oxide cross-linked acidic polyionic liquid, belonging to the technical field of solid acid catalysis. The catalyst prepared by the present disclosure has good Lewis acid site and Brönsted acid site, and has the characteristics of high speed, high efficiency, environment friendliness and the like when catalyzing preparation of furfural from xylose. The catalyst has the advantages of easy separation, multiple cycles of recycling and the like, and is green and pollution-free. The magnetic metal oxide cross-linked acidic polyionic liquid prepared by using the present disclosure has the characteristics of high speed, high effi- (Continued)

ciency, environment friendliness and the like when catalyzing preparation of furfural from xylose, and meanwhile, the catalyst has the advantages of easy separation, multiple cycles of recycling and the like, and is green and pollution-free.

17 Claims, 4 Drawing Sheets

(51) Int. Cl.
| | |
|---|---|
| *C07D 307/50* | (2006.01) |
| *B01J 37/06* | (2006.01) |
| *B01J 35/00* | (2006.01) |
| *B01J 37/00* | (2006.01) |
| *B01J 23/835* | (2006.01) |
| *C08F 226/06* | (2006.01) |
| *B01J 23/745* | (2006.01) |
| *B01J 31/00* | (2006.01) |
| *C08F 292/00* | (2006.01) |
| *B01J 31/06* | (2006.01) |
| B01J 21/04 | (2006.01) |
| B01J 21/08 | (2006.01) |
| B01J 21/06 | (2006.01) |

(52) U.S. Cl.
CPC ............ *B01J 31/00* (2013.01); *B01J 31/0289* (2013.01); *B01J 31/06* (2013.01); *B01J 35/0033* (2013.01); *B01J 37/009* (2013.01); *B01J 37/06* (2013.01); *B01J 37/08* (2013.01); *C07D 307/50* (2013.01); *C08F 226/06* (2013.01); *C08F 292/00* (2013.01); *B01J 21/04* (2013.01); *B01J 21/063* (2013.01); *B01J 21/066* (2013.01); *B01J 21/08* (2013.01); *B01J 31/0239* (2013.01); *B01J 31/0254* (2013.01); *B01J 2231/70* (2013.01)

(58) Field of Classification Search
CPC .. B01J 31/0239; B01J 31/0289; B01J 23/745; C07D 307/50
See application file for complete search history.

(56) References Cited

OTHER PUBLICATIONS

Pourjavadi et al., Crosslinked poly(ionic liquid) as high loaded dual acidic organocatalyst, Journal of Molecular Catalysis A: Chemical, 365 (2012) 55-59.*
Zheng et al., Poly(ionic liquid) immobilized magnetic nanoparticles as newadsorbent for extraction and enrichment of organophosphoruspesticides from tea drinks, Journal of Chromatography A 1358 (2014) 39-45.*
Liu et al., Polymeric ionic liquid (PIL)-supported recyclable catalysts for biomass conversion into HMF, Biomass and Bioenergy 48 (2013) 181-190.*
Xin et al., Imidazolium-based ionic liquids grafted on solid surfaces, Chem. Soc. Rev., 2014, vol. 43 pp. 7171-7187.*
Pizzoccaro et al., Design of phosphonated Imidazolium-based inoic liquids grafted on Gamma-alumina: potential model for hydrbid memebranes, International Journal of Molecular Science, 2016, vol. 17, 1212.*
Shanshan Yin et al., Magnetic material grafted cross-linked imidazolium based polyionic liquids: an efficient acid catalyst for the synthesis of promising liquid fuel 5-ethoxymethylfurfural from carbohydrates, Journal of Materials Chemistry A, Feb. 2, 2015(Feb. 2, 2015), No. 9, vol. 3, ISSN:2050-7488, pp. 4992-4999.
Paolo Agrigento et al., Magnetic material grafted cross-linked imidazolium based polyionic liquids: an efficient acid catalyst for the synthesis of Highly cross-linked imidazolium salt entrapped magnetic particles-preparation and applications, Journal of Materials Chemistry, Aug. 14, 2012(Aug. 14, 2012), No. 38, vol. 22, ISSN:0959-9428, pp. 20728-20735.
Ali Pourjavadi et al., Multi-Layer Functionalized Poly(Ionic Liquid) Coated Magnetic Nanoparticles: Highly Recoverable and Magnetically Separable Bronsted Acid, ACS Catalysis, May 10, 2012(May 10, 2012), No. 6, Vo. 2, ISSN:2155-5435, pp. 1259-1266.

* cited by examiner

PREPARATION AND APPLICATION OF MAGNETIC METALLIC OXIDE CROSS-LINKED ACIDIC POLYIONIC LIQUID

TECHNICAL FIELD

The disclosure herein relates to the preparation and application of magnetic metallic oxide cross-linked acidic polyionic liquid, and belongs to the field of solid acid catalysis.

BACKGROUND

With the development of the world economy, the rapid increase of the world population and the improvement of people's living standards, energy consumption continues to increase, and the reserves of traditional fossil energy (coal, oil and natural gas) are gradually decreasing. At the same time, the impact of fossil energy on environmental pollution and the global climate is growing. Therefore, finding novel renewable energies to alleviate the energy crisis is urgent, and it is also a hot spot of current research. Solar energy, water energy, wind energy, geothermal energy and biomass energy have all been studied, and they are expected to alleviate the shortage of energy. Biomass energy is the only sustainable organic carbon source on the earth, and it has the advantages of abundant reserves, wide distribution, renewability, low pollution, etc. While sugar is the foundation of biomass energy, it can be used to prepare a variety of platform compounds. Therefore, people have more in-depth research on sugar.

Furfural, also known as 2-furaldehyde, is a highly valued derivative of the furan ring system. Since furfural has an aldehyde group and a dienyl ether functional group, furfural has the properties of the aldehydes, ethers and diener, and particularly has similar properties to benzaldehyde. The chemical properties of furfural are very active, so that the furfural can be synthesized into a variety of different derivatives by oxidation, condensation, etc. These derivatives also have the properties of a platform compound and can be used in the manufacture of plastics, pharmaceuticals, pesticides and other industries in the form of intermediate substances.

For the preparation of furfural, the research mainly focuses on xylose, which is a component of xylan, and xylan is widely present in plants, and thus, has research value. Taking the conversion of xylose to furfural as an example, xylose is firstly isomerized to xylulose under the action of an acidic catalyst, and the xylulose is dehydrated to form furfural.

At present, the Lewis acid/ionic liquid system is widely concerned, but the disadvantage of this system is that the ionic liquid is difficult to recycle after the reaction, and it is easy to cause environmental pollution. With the gradual deepening of research, many researchers agree that ionic liquids are not only solvents in biomass conversion, but also excellent catalysts. Therefore, the ionic liquid and the substance having the Lewis acid site are immobilized into a heterogeneous catalyst by functionalization, which has a good catalytic effect on the catalytic preparation of furfural from xylose. At the same time, such a catalyst is beneficial for recycling, embodying the purpose of green chemistry and having broad application prospects.

It has been reported that $SiO_2$—$Al_2O_3$ is used as a catalyst to catalyze the conversion of xylose to furfural, and the conversion rate of xylose can reach 89.2%, but the yield of furfural is only 32.9%. Another report uses $Fe_3O_4$—$SiO_2$—$SO_3H$ to catalyze xylose to prepare furfural, but the yield of furfural is only 38%. It can be seen that when the catalyst contains only Lewis acid or only Brönsted acid, the yield of furfural is relatively low; under the optimal conditions, when the xylose is only catalyzed by the metal oxide support, the conversion rate of xylose reaches 85%-93%, but the yield of furfural is only 33%-42%; and when only catalyzed by sulfated divinylimidazole, the conversion rate of xylose reaches 75%, the yield of furfural is 48%, and meanwhile, a large amount of humin is formed, which is not conducive to the separation of furfural after the reaction. In summary, a large number of documents have been reported the use of acidic catalysts to catalyze the preparation of furfural from xylose, but most heterogeneous solid acid catalysts obtain a low yield of furfural and the reaction conditions is not mild enough when used for catalyzing the conversion of xylose to furfural.

SUMMARY

In order to overcome the shortcomings and deficiencies of the prior art, an object of the present disclosure is to synthesize a novel magnetic metal oxide cross-linked acidic polyionic liquid and application thereof to catalyze the preparation of furfural from xylose. In the method for catalyzing the production of furfural from xylose based on a magnetic metal oxide immobilized cross-linked acidic polyionic liquid according to the present disclosure, the conversion rate of xylose is up to 97%, and the yield of furfural is up to 72%. The catalyst used has the advantages of easy separation and simple preparation method, and the catalyst still has good catalytic activity after being recycled for 5 times, thereby realizing the repeated use of the catalyst, and embodying the purpose of green sustainable development.

A first object of the present disclosure is to provide a magnetic metal oxide cross-linked acidic polyionic liquid which is obtained by the following steps: after thiolation of a metal oxide support, crosslinking with divinylimidazole halide under the action of an initiator to obtain a metal oxide cross-linked polyionic liquid, then wrapping magnetic nanoparticles with the metal oxide cross-linked polyionic liquid to obtain a magnetic metal oxide cross-linked polyionic liquid, and reacting the magnetic oxide cross-linked polyionic liquid with concentrated acid to obtain the magnetic metal oxide cross-linked acidic polyionic liquid.

In one embodiment, the metal oxide support may be $\gamma$-$Al_2O_3$, $ZrO_2$, $TiO_2$, $SnO_2$, or the like.

In one embodiment, the thiolation of the metal oxide support comprises: reacting the metal oxide support with $\gamma$-mercaptopropyltrimethoxysilane in an organic solvent in an oil bath under an inert gas, cooling, filtering, washing and drying to obtain a thiolated metal oxide support.

In one embodiment, the initiator may be azobisisobutyronitrile, azobisvaleronitrile, dimethyl azobisisobutyrate, or the like.

In one embodiment, the divinylimidazole halide is obtained by reacting 1-vinylimidazole with 1,2-dibromoethane, dichloroethane or diiodoethane.

In one embodiment, the preparation of the divinylimidazole halide specifically comprises: weighing 1-vinylimidazole and 1,2-dihaloethane (e.g., 1,2-dibromoethane, dichloroethane or diiodoethane), adding a toluene solvent, reacting in an oil bath, filtering out the solid, dissolving the solid in methanol, decolorizing by activated carbon, filtering, carrying out rotary evaporation, and drying to respectively obtain the divinylimidazole halide.

In one embodiment, the metal oxide cross-linked polyionic liquid is specifically prepared by the following steps: under the action of the initiator, reacting the thiolated metal oxide support and the divinylimidazole halide in a methanol solvent in an oil bath under an inert condition, cooling to room temperature, filtering, washing with alcohol, and drying to obtain the metal oxide cross-linked polyionic liquid.

In one embodiment, the magnetic nanoparticles are $Fe_3O_4$ nanoparticles.

In one embodiment, the preparation of the $Fe_3O_4$ nanoparticles may comprise: dissolving iron chloride hexahydrate and ferrous sulfate heptahydrate in deionized water, dropwisely adding ammonia water (28 wt %) to adjust the pH of the solution, stirring in a water bath, cooling to room temperature, separating the black precipitate by a magnet, washing sequentially with ethanol and water, and vacuum-drying to obtain the $Fe_3O_4$ nanoparticles.

In one embodiment, the wrapping the $Fe_3O_4$ nanoparticles with the metal oxide cross-linked polyionic liquid comprises: dispersing the $Fe_3O_4$ and the metal oxide cross-linked polyionic liquid in ethanol, stirring vigorously in a water bath, cooling to room temperature, carrying out magnetic separation, washing with alcohol, and drying to obtain the magnetic metal oxide cross-linked polyionic liquid.

In one embodiment, the magnetic metal oxide cross-linked acidic polyionic liquid is specifically prepared by the following steps: dispersing the magnetic metal oxide cross-linked polyionic liquid in deionized water, dropwisely adding concentrated acid under an ice bath condition, stirring at room temperature in a water bath, filtering, washing with water, and drying to obtain the magnetic metal oxide cross-linked acidic polyionic liquid (i.e., solid acid catalyst).

In one embodiment, the concentrated acid may be concentrated hydrochloric acid, concentrated nitric acid, concentrated phosphoric acid, concentrated sulfuric acid, or the like.

In one embodiment, the preparation of the magnetic metal oxide cross-linked acidic polyionic liquid specifically comprises:

(1) synthesizing divinylimidazole halide;

(2) thiolation of metal oxide support: reacting the metal oxide support with γ-mercaptopropyltrimethoxysilane in a toluene solvent in an oil bath under an inert condition, cooling to room temperature, filtering, washing with alcohol, and drying to obtain the thiolated metal oxide support;

(3) under the action of the initiator, reacting the thiolated metal oxide support and the divinylimidazole halide in a methanol solvent in an oil bath under an inert condition, cooling to room temperature, filtering, washing with alcohol, and drying to obtain the metal oxide cross-linked polyionic liquid;

(4) wrapping $Fe_3O_4$ nanoparticles with metal oxide cross-linked polyionic liquid: dispersing the $Fe_3O_4$ and the metal oxide cross-linked polyionic liquid in ethanol, stirring vigorously in a water bath, cooling to room temperature, carrying out magnetic separation, washing with alcohol, and drying to obtain the magnetic metal oxide cross-linked polyionic liquid; and (5) magnetic metal oxide cross-linked acidic polyionic liquid: dispersing the magnetic metal oxide cross-linked polyionic liquid in deionized water, dropwisely adding concentrated acid under an ice bath condition, stirring at room temperature in a water bath, filtering, washing with water, and drying to obtain the magnetic metal oxide cross-linked acidic polyionic liquid.

In one embodiment, the γ-$Al_2O_3$ may be prepared by a sol-gel process, for example: preparing a cetyltrimethylammonium bromide (CTAB) aqueous solution, respectively dissolving aluminum nitrate and ammonium bicarbonate in the CTAB solution, slowly and dropwisely adding the ammonium bicarbonate solution to the vigorously stirred aluminum nitrate solution until the reaction solution exhibits a turbid sol, and stopping the addition; and continuing stirring for aging, vacuum-drying to obtain a dried gel powder, and calcining in a muffle furnace to obtain the γ-$Al_2O_3$ nanoparticles.

In one embodiment, the $ZrO_2$ may be prepared by a precipitation process: dissolving zirconium oxychloride octahydrate in deionized water, dropwisely adding 28% concentrated ammonia water under stirring to the complete precipitation, carrying out suction filtration, washing with deionized water until neutral, drying, and calcining in a muffle furnace to obtain the $ZrO_2$ nanoparticles.

In one embodiment, the $TiO_2$ may be prepared by a sol-gel process: dissolving hexadecylamine in ethanol, dropwisely adding a 0.1 mol/L potassium chloride solution, adding titanium tetraisopropoxide, vigorously stirring the mixture in a water bath, carrying out suction filtration, washing with alcohol and drying to obtain the $TiO_2$ nanoparticles.

In one embodiment, the $SnO_2$ may be prepared by a sol-gel process: adding deionized water and polyethylene glycol into a hydrothermal kettle, adding tin chloride and 28% concentrated ammonia water, carrying out hydrothermal treatment, cooling to room temperature, carrying out suction filtration, washing with water, washing with alcohol, and drying to obtain the $SnO_2$ nanoparticles.

A second object of the present disclosure is to provide a magnetic metal oxide cross-linked acidic polyionic liquid which is prepared by the above method.

In one embodiment of the present disclosure, the magnetic metal oxide cross-linked acidic polyionic liquid is prepared by the following steps: after thiolation of a metal oxide support, crosslinking with divinylimidazole halide under the action of an initiator to obtain a metal oxide cross-linked polyionic liquid, then wrapping magnetic nanoparticles with the metal oxide cross-linked polyionic liquid to obtain a magnetic metal oxide cross-linked polyionic liquid, and reacting the magnetic oxide cross-linked polyionic liquid with concentrated acid to obtain the magnetic metal oxide cross-linked acidic polyionic liquid.

A third object of the present disclosure is to provide application of the magnetic oxide cross-linked acidic polyionic liquid.

In one embodiment, the application is to catalyze the preparation of furfural from xylose.

A fourth object of the present disclosure is to provide a method for preparing furfural, which uses the magnetic metal oxide cross-linked acidic polyionic liquid as a catalyst to catalyze the production of furfural from xylose.

In one embodiment, the method comprises placing xylose and a magnetic metal oxide cross-linked acidic polyionic liquid catalyst into a reactor in a mass ratio of 1:(0.3-0.7), and adding a reaction solvent to react.

In one embodiment, the reaction solvent is any one or a combination of two or more of DMSO, DMF, DMA, NMP, THF, 2-MTHF, toluene and n-butanol.

In one embodiment, the addition ratio of the xylose to the reaction solvent is 100 mg: (1-5 mL).

In one embodiment, the reaction is carried out at 120° C.-160° C. for 1-5 h.

In one embodiment, the reaction is carried out in an oil bath.

In one embodiment, the method specifically comprises:

(1) placing xylose and a magnetic metal oxide cross-linked acidic polyionic liquid catalyst in a reactor in a mass ratio of 1:(0.3-0.7), adding a reaction solvent, reacting at 120° C.-160° C. in an oil bath for 1-5 h, and cooling after the reaction is finished;

(2) after the reaction solution in step (1) is cooled, diluting a certain amount of the reaction solution with deionized water to the specified volume, and determining the conversion rate of xylose and the yield of furfural by a high-performance liquid chromatograph; and (3) after the reaction in step (1) is finished, separating out the catalyst by the action of an external magnetic field, washing with alcohol, and drying to be re-added to the reaction system of step (1).

The present disclosure has the following advantages and effects:

(1) The magnetic metal oxide cross-linked acidic polyionic liquid of the present disclosure is a heterogeneous solid acid catalyst, which not only has a good catalytic effect on the conversion of xylose into furfural, but also still has good catalytic activity after repeated use.

(2) The magnetic metal oxide cross-linked acidic polyionic liquid of the present disclosure is a magnetic solid acid catalyst. After the reaction, it can be easily separated and recycled by the action of an external magnetic field, thereby embodying the green chemical policy.

(3) The metal oxide support of the present disclosure has a good Lewis acid site, which plays a vital role in the isomerization of xylose, and can significantly increase the conversion rate of xylose and the yield of furfural.

(4) The acidic polyionic liquid of the present disclosure has a good Brönsted acid site, and plays a good role in dehydration of xylose to furfural, and crosslinking it with an oxide support can achieve good catalytic effect and is conducive to the recycling after the reaction, thereby adhering to the purpose of green sustainable development.

(5) When the magnetic metal oxide cross-linked acidic polyionic liquid of the present disclosure is utilized to catalyze the production of furfural from xylose, and almost no humin is formed in the reaction system, which is favorable for the separation of furfural after the reaction. In addition, the conversion rate of xylose can reach 97%, the yield of furfural can reach 72%, and the catalyst performance is only reduced by 4%-12% after 5 cycles.

DETAILED DESCRIPTION

The following is a detailed description of the present disclosure.

Conversion Rate of Xylose:

$$\text{Xylose conversion (mol \%)} = \left(1 - \frac{\text{moles of remaining xylose}}{\text{moles of starting xylose}}\right) \times 100\%$$

Yield of Furfural:

$$\text{Furfural yield (mol \%)} = \left(\frac{\text{moles of furfural}}{\text{moles of starting xylose}}\right) \times 100\%$$

Example 1: Synthesis of Divinylimidazole Halide 1-vinylimidazole and 1,2-dibromoethane, dichloroethane or diiodoethane were weighed, a toluene solvent was added to react in an oil bath, the solid was filtered out and dissolved in methanol, decolorization was carried out by activated carbon, filtration and rotary evaporation were carried out, and drying was carried out to obtain the divinylimidazole halide.

Figure 1:
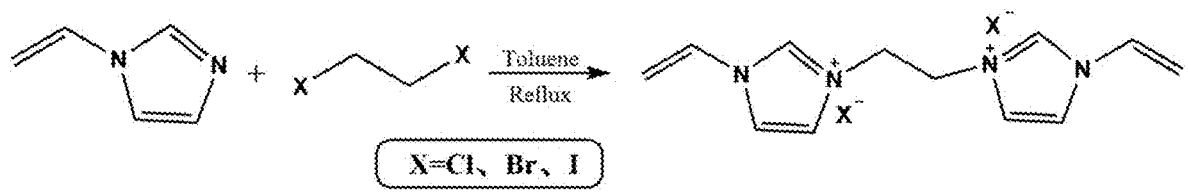
FIG. 1 is a synthetic route of divinylimidazolium halide.

The synthetic route is shown in FIG. 1.

Figure 2:
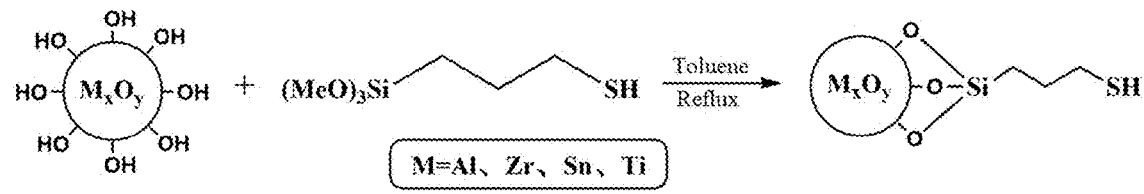
FIG. 2 is a preparation route of a thiol-modified metal oxide support.
Figure 3:
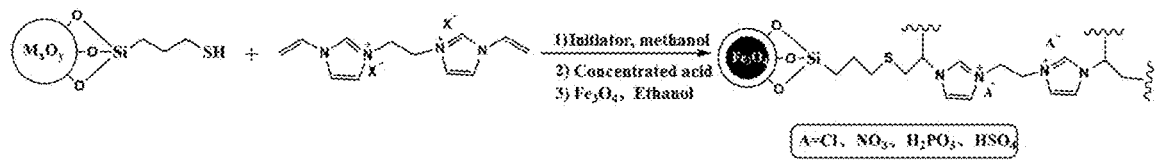
FIG. 3 is preparation of a magnetic metal oxide support immobilized cross-linked acidic polyionic liquid.

Example 2: Preparation of Magnetic Metal Oxide Cross-Linked Acidic Polyionic Liquid The preparation route of the magnetic metal oxide cross-linked acidic polyionic liquid is shown in FIGS. 2-3.

(1) Divinylimidazole halide was taken;

(2) thiolation of metal oxide support: the metal oxide support was reacted with γ-mercaptopropyltrimethoxysilane in a toluene solvent in an oil bath under an inert condition, and after the reaction was cooled to room temperature, filtering and washing with alcohol were carried, and drying was performed to obtain the thiolated metal oxide support;

(3) under the action of the initiator, the thiolated metal oxide support was reacted with the divinylimidazole halide in a methanol solvent in an oil bath under an inert condition, and after the reaction was cooled to room temperature, filtering and washing with alcohol were carried, and drying was carried out to obtain the metal oxide cross-linked polyionic liquid;

(4) wrapping ferroferric oxide nanoparticles with metal oxide cross-linked polyionic liquid: the ferroferric oxide and the metal oxide cross-linked polyionic liquid were dispersed in ethanol, and stirred vigorously in a water bath, and the mixture was cooled to room temperature, magnetically separated, washed with alcohol, and dried to obtain the magnetic metal oxide cross-linked polyionic liquid; and (5) magnetic metal oxide cross-linked acidic polyionic liquid: the magnetic metal oxide cross-linked polyionic liquid was dispersed in deionized water, concentrated sulfuric acid was dropwisely added under an ice bath condition, and the mixture was stirred at room temperature in a water bath, filtered, washed with water, and dried to obtain the magnetic metal oxide cross-linked acidic polyionic liquid.

The oxide support was γ—$Al_2O_3$, $ZrO_2$, $TiO_2$ or $SnO_2$, and the obtained magnetic metal oxide cross-linked acidic polyionic liquid was $Fe_3O_4@Al_2O_3$-SH-IM-$HSO_4$, $Fe_3O_4@ZrO_2$-SH-IM-$HSO_4$, $Fe_3O_4@TiO_2$-SH-IM-$HSO_4$ or $Fe_3O_4@SnO_2$-SH-IM-$HSO_4$.

Example 3: Production of Furfural from Xylose Using Magnetic Metal Oxide Cross-Linked Acidic Polyionic Liquid as Catalyst Similar to the method of Example 2, γ-$Al_2O_3$ was selected as the oxide support, and the concentrated sulfuric acid in step (5) was replaced with concentrated hydrochloric acid, concentrated nitric acid or concentrated phosphoric acid to obtain the magnetic metal oxide cross-linked acidic polyionic liquid $Fe_3O_4@Al_2O_3$-SH-IM-Cl, $Fe_3O_4@Al_2O_3$-SH-IM-$NO_3$ or $Fe_3O_4@Al_2O_3$-SH-IM-$H_2PO_3$. The properties of the products obtained with different concentrated acids were compared. The method was as follows:

(1) 50 mg of magnetic metal oxide cross-linked acidic polyionic liquid ($Fe_3O_4@Al_2O_3$-SH-IM-Cl, $Fe_3O_4@Al_2O_3$-SH-IM-$NO_3$, $Fe_3O_4@Al_2O_3$-SH-IM-$H_2PO_3$ or $Fe_3O_4@Al_2O_3$-SH-IM-F—$HSO_4$) was weighed and added to a reactor containing 3 mL of DMSO;

(2) 100 mg of xylose was weighed in the reaction system of step (1), and stirred in an oil bath at 140° C. for 3 h, and the reaction product was taken out and cooled after the reaction was finished; and (3) after the reaction product was cooled, 50 μL of sample was taken and diluted to 5 mL with deionized water, and the yield of furfural was determined by a high-performance liquid chromatograph.

It was determined that under the catalytic action of the $Fe_3O_4@Al_2O_3$-SH-IM-Cl, $Fe_3O_4@Al_2O_3$-SH-IM-$NO_3$, $Fe_3O_4@Al_2O_3$-SH-IM-$H_2PO_3$ and $Fe_3O_4@Al_2O_3$-SH-IM-F—$HSO_4$, the yield of furfural was respectively 42%, 43%, 55% and 72%.

Figure 4:
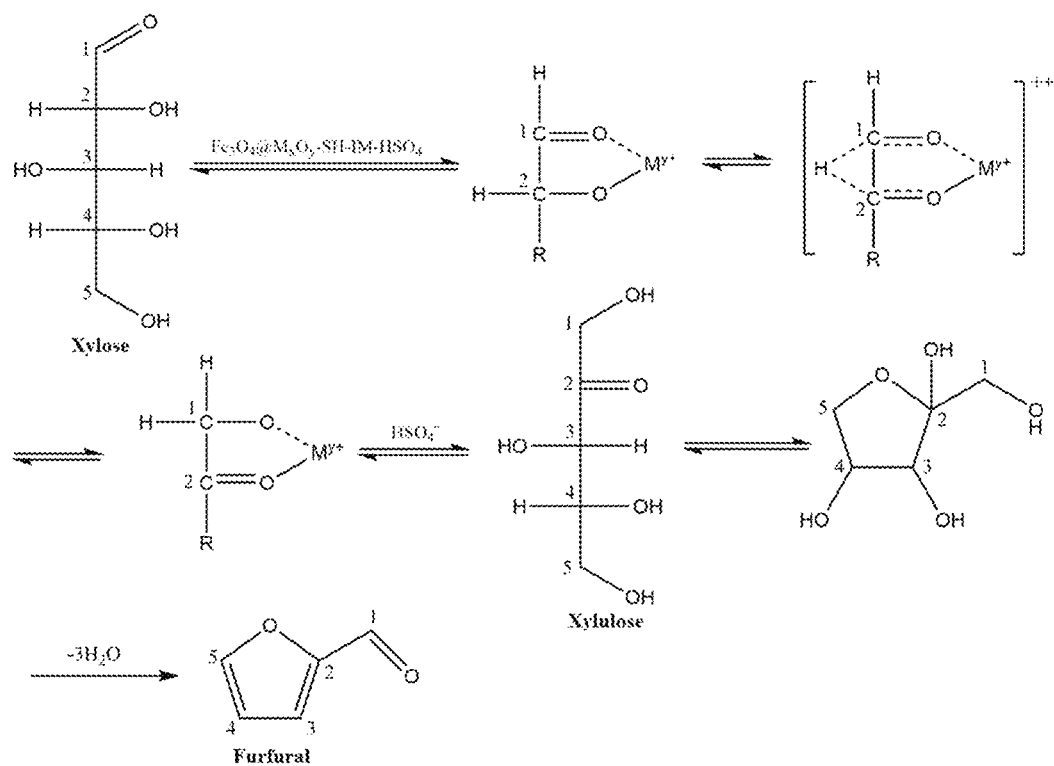
FIG. 4 is a reaction diagram of production of furfural from xylose using the magnetic metal oxide cross-linked acidic polyionic liquid as a catalyst.

Example 4: Production of Furfural from Xylose Using $Fe_3O_4@Al_2O_3$-SH-IM-$HSO_4$ as Catalyst FIG. 4 is a possible reaction diagram of production of furfural from xylose using the magnetic metal oxide cross-linked acidic polyionic liquid as a catalyst.

(1) 50 mg of magnetic metal oxide cross-linked acidic polyionic liquid ($Fe_3O_4@Al_2O_3$-SH-IM-$HSO_4$) was weighed and added into a reactor containing 3 mL of DMSO, toluene or n-butanol;

(2) 100 mg of xylose was weighed in the reaction system of step (1), and stirred in an oil bath at 140° C. for 3 h, and the reaction product was taken out and cooled after the reaction was finished; and (3) after the reaction product was cooled, 50 μL of sample was taken and diluted to 5 mL with deionized water, and the yield of furfural was determined by a high-performance liquid chromatograph.

It was determined that in the DMSO, toluene and n-butanol, the yield of furfural was respectively 72%, 58% and 56%.

Example 5: Production of Furfural from Xylose Using $Fe_3O_4@Al_2O_3$-SH-IM-$HSO_4$ as Catalyst (1) 30-70 mg of magnetic metal oxide cross-linked acidic polyionic liquid ($Fe_3O_4@Al_2O_3$-SH-IM-$HSO_4$) was weighed and respectively added into a reactor containing 3 mL of DMSO;

(2) 100 mg of xylose was weighed in the reaction system of step (1), and stirred in an oil bath at 140° C. for 3 h, and the reaction was taken out and cooled after the reaction was finished; and (3) after the reaction product was cooled, 50 μL of sample was taken and diluted to 5 mL with deionized water, and the yield of furfural was determined by a high-performance liquid chromatograph.

It was determined that when the amount of the solid acid catalyst was respectively 30, 40, 50, 60 and 70 mg, the yield of furfural was respectively 48%, 63%, 72%, 70% and 65%.

After the reaction of Example 4 was finished, the solid acid catalyst under the optimum conditions was magnetically separated out, cleaned, dried, and added to the optimum experimental conditions in the examples for repeated calculation. It was experimentally calculated that after the solid acid catalyst was recycled 5 times, the yield of furfural was still up to 63%.

Example 7

(1) 50 mg of magnetic metal oxide cross-linked acidic polyionic liquid ($Fe_3O_4@Al_2O_3$-SH-IM-$HSO_4$) was weighed and added into a reactor containing 3 mL of DMSO;

(2) the DMSO in step (1) was replaced with another organic solvent such as DMF, DMA, NMP, THF, 2-MTHF, toluene or n-butanol.

(3) 100 mg of xylose was weighed in the reaction system of step (1) and step (2), and stirred in an oil bath at 140° C. for 3 h, and the reaction product was taken out and cooled after the reaction was finished; and (4) after the reaction product was cooled, 50 μL of sample was taken and diluted to 5 mL with deionized water, and the yield of furfural was determined by a high-performance liquid chromatograph.

Figure 5:
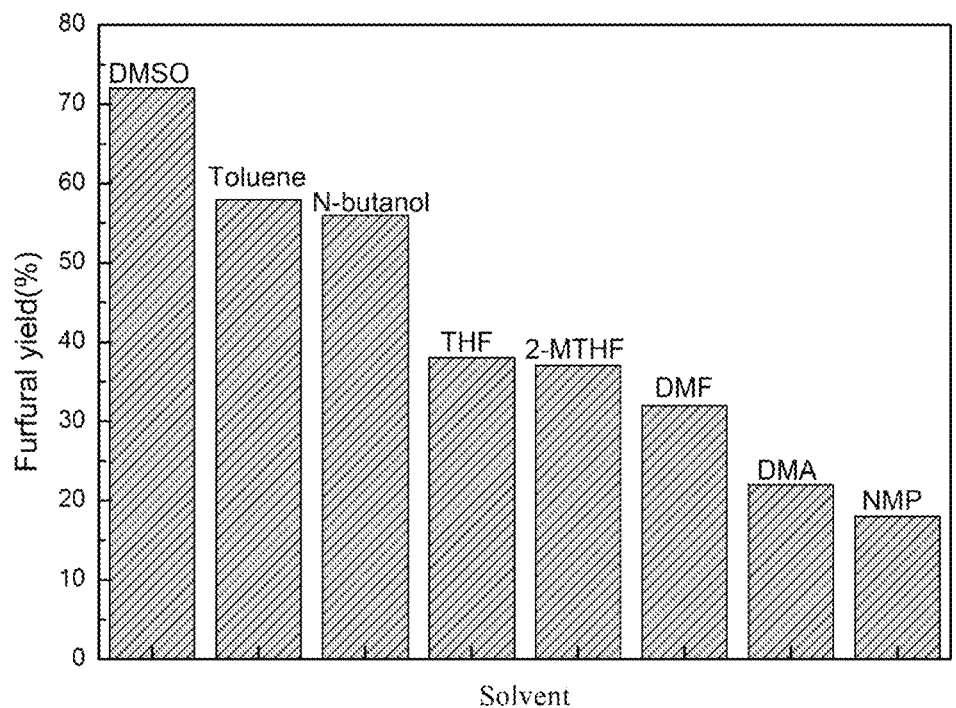
FIG. 5 is a graph showing the yield of the solid acid catalyst in Example 7 catalyzing the xylose reaction in different solvents.

After the determination, the results as shown in FIG. 5. In DMSO, DMF, DMA, NMP, THF, 2-MTHF, toluene and n-butanol, the yield of furfural was respectively 72%, 32%, 22%, 21%, 38%, 37%, 58% and 56%.

Example 8

(1) 50 mg of magnetic metal oxide cross-linked acidic polyionic liquid ($Fe_3O_4@Al_2O_3$-SH-IM-$HSO_4$) was weighed and added into reactors respectively containing 1, 2, 3, 4 and 5 mL of DMSO;

(2) 100 mg of xylose was weighed in the reaction system of step (1), and stirred in an oil bath at 140° C. for 3 h, and the reaction product was taken out and cooled after the reaction was finished; and (3) after the reaction product was cooled, 50 μL of sample was taken and diluted to 5 mL with deionized water, and the yield of furfural was determined by a high-performance liquid chromatograph.

Figure 6:
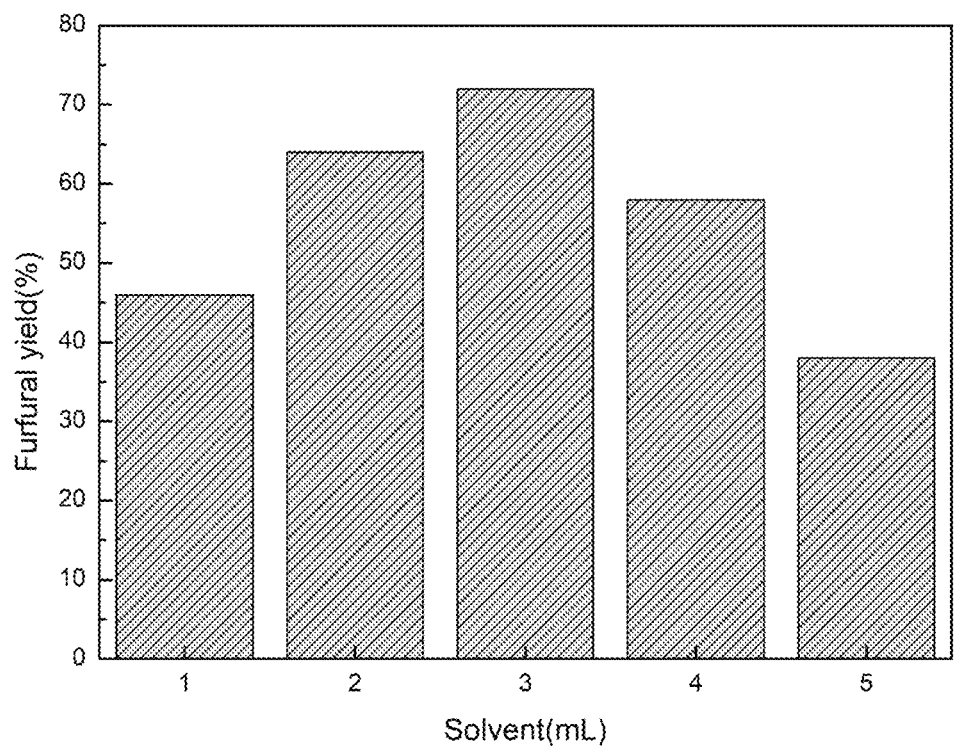
FIG. 6 is a graph showing the yield of the solid acid catalyst in Example 8 catalyzing the xylose reaction in different solvent amounts.

After the determination, the results are shown in FIG. 6. When the solvent amount was respectively 1, 2, 3, 4 and 5 mL, the yield of furfural was respectively 46%, 64%, 72%, 55% and 38%.

Example 9

(1) 50 mg of magnetic metal oxide cross-linked acidic polyionic liquid ($Fe_3O_4@Al_2O_3$-SH-IM-$HSO_4$) was weighed and added into a reactor containing 3 mL of DMSO;

(2) 100 mg of xylose was weighed in the reaction system of step (1), and stirred in an oil bath at 110-160° C. for 3 h, and the reaction product was taken out and cooled after the reaction was finished; and (3) after the reaction product was cooled, 50 µL of sample was taken and diluted to 5 mL with deionized water, and the yield of furfural was determined by a high-performance liquid chromatograph.

Figure 7:
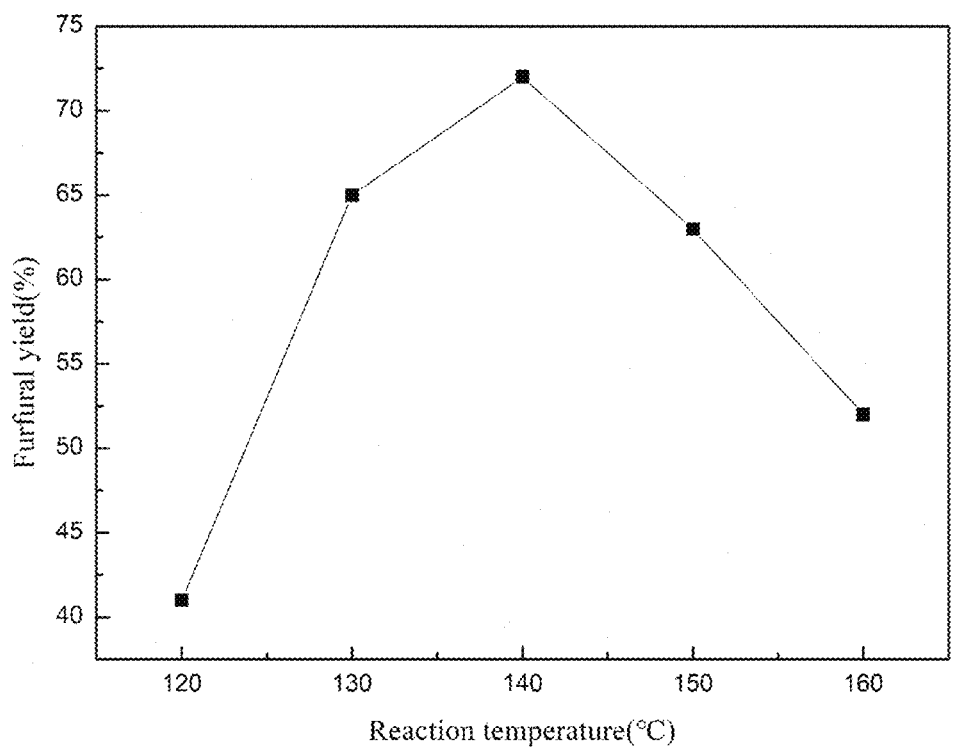
FIG. 7 is a graph showing the yield of the solid acid catalyst in Example 9 catalyzing the xylose reaction at different temperatures.

After the determination, the results are shown in FIG. 7. At a temperature gradient of 120-160° C., the yield of furfural was respectively 41%, 65%, 72%, 63% and 52%.

Example 10

(1) 50 mg of magnetic metal oxide cross-linked acidic polyionic liquid ($Fe_3O_4@Al_2O_3$-SH-IM-$HSO_4$) was weighed and added into a reactor containing 3 mL of DMSO;

(2) 100 mg of xylose was weighed in the reaction system of step (1), and stirred in an oil bath at 140° C. for a temperature gradient of 1-5 h, and the reaction product was taken out and cooled after the reaction was finished; and (3) after the reaction was cooled, 50 µL of sample was taken and diluted to 5 mL with deionized water, and the yield of furfural was determined by a high-performance liquid chromatograph.

Figure 8:
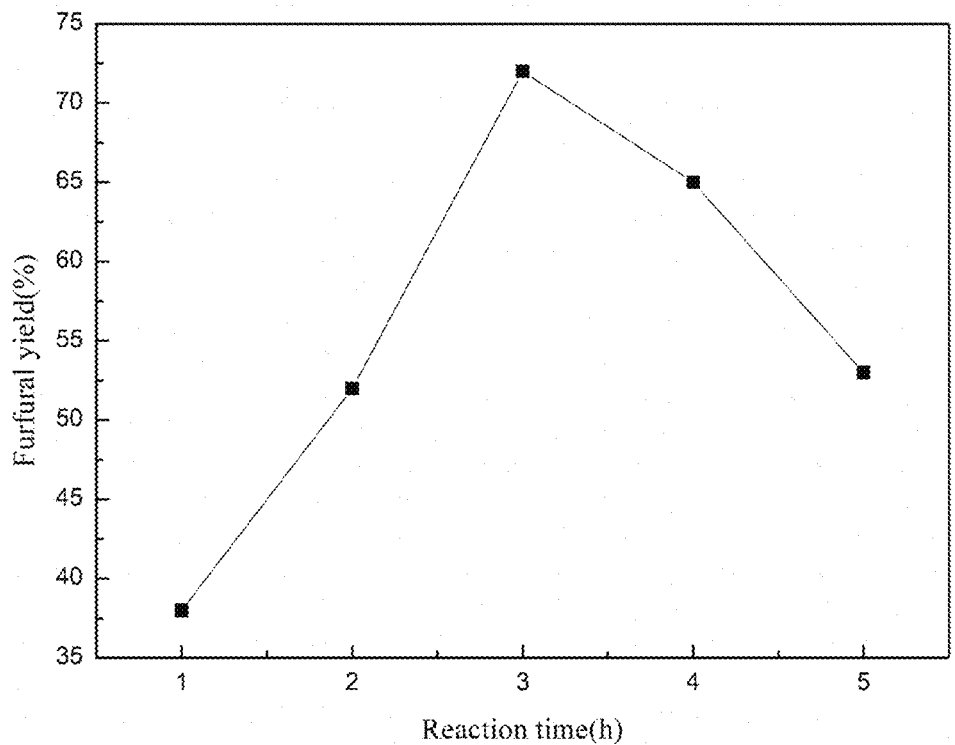
FIG. 8 is a graph showing the yield of the solid acid catalyst in Example 10 catalyzing the xylose reaction at different times.

After the determination, the results are shown in FIG. 8. When the reaction temperature was respectively 1, 2, 3, 4 and 5 h, the yield of furfural was respectively 38%, 52%, 72%, 65% and 53%.

Example 11

(1) 30, 40, 50, 60 and 70 mg of magnetic metal oxide cross-linked acidic polyionic liquid ($Fe_3O_4@Al_2O_3$-SH-IM-$HSO_4$) were weighed and respectively added into reactors containing 3 mL of DMSO;

(2) 100 mg of xylose was weighed in the reaction system of step (1), and stirred in an oil bath at 140° C. for 3 h, and the reaction product was taken out and cooled after the reaction was finished; and (3) after the reaction product was cooled, 50 µL of sample was taken and diluted to 5 mL with deionized water, and the yield of furfural was determined by a high-performance liquid chromatograph.

Figure 9:
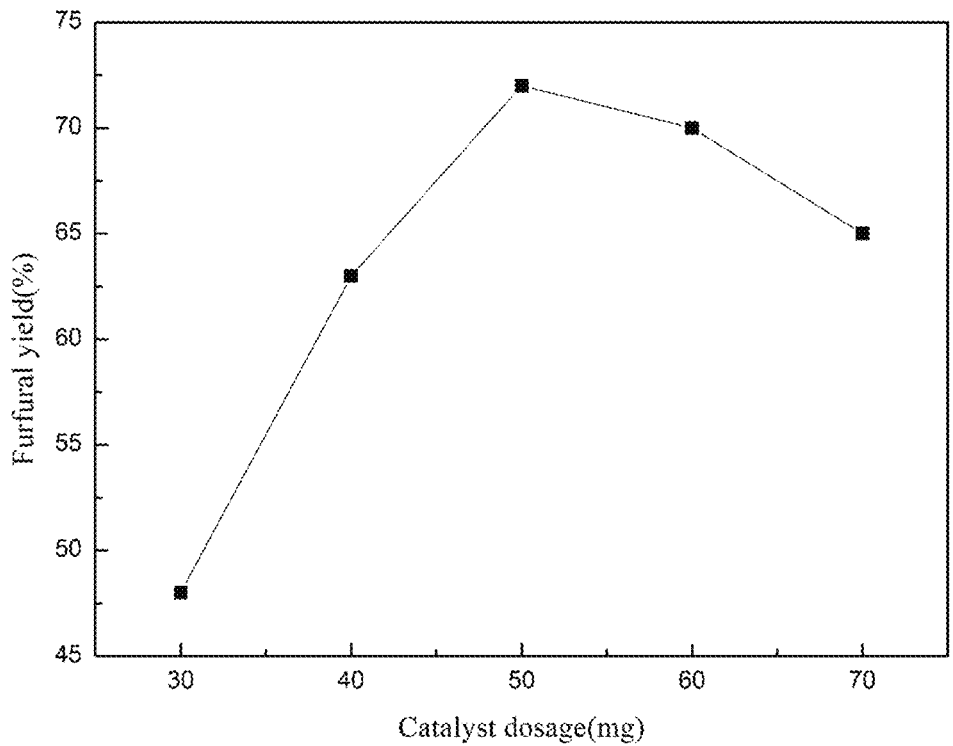
FIG. 9 is a graph showing the yield of the solid acid catalyst in Example 11 catalyzing the xylose reaction at different catalyst amounts.

After determination, the results are shown in FIG. 9. When the solid acid catalyst amount was respectively 30, 40, 50, 60 and 70 mg, the yield of furfural was respectively 48%, 63%, 72%, 70% and 65%.

After the reaction of Example 5 was finished, the solid acid catalyst under the optimum conditions was magnetically separated out, cleaned, dried, and added to the optimum experimental conditions in the examples for repeated calculation. It was experimentally calculated that after the solid acid catalyst was recycled 5 times, the yield of furfural was still up to 63%.

Example 12: Preparation of Magnetic Metal Oxide Cross-Linked Acidic Polyionic Liquid ($Fe_3O_4@M_xO_y$-SH-IM-$HSO_4$)

The preparation of the magnetic metal oxide cross-linked acidic polyionic liquid was carried out by the following steps:

(1) Synthesis of divinylimidazole halide: 1-vinylimidazole and 1,2-haloethane were weighed, a toluene solvent was added to react in an oil bath, the solid was filtered out and dissolved in methanol, decolorization was carried out by activated carbon, filtration and rotary evaporation were carried out, and drying was carried out to obtain the divinylimidazole halide.

(2) Thiolation of metal oxide support: the support was reacted with γ-mercaptopropyltrimethoxysilane in a toluene solvent in an oil bath under an inert condition, and after the reaction was cooled to room temperature, filtering and washing with alcohol were carried, and drying was carried out to obtain the thiolated metal oxide support.

(3) Under the action of the initiator azodiisobutyronitrile, the thiolated metal oxide support was reacted with the divinylimidazole halide in a methanol solvent in an oil bath under an inert condition, and after the reaction was cooled to room temperature, filtering and washing with alcohol were carried, and drying was carried out to obtain the metal oxide cross-linked polyionic liquid.

(4) Wrapping $Fe_3O_4$ nanoparticles with metal oxide cross-linked polyionic liquid: the $Fe_3O_4$ and the metal oxide cross-linked polyionic liquid were dispersed in ethanol and stirred vigorously in a water bath, and the mixture was cooled to room temperature, magnetically separated, washed with alcohol, and dried to obtain the magnetic metal oxide cross-linked polyionic liquid.

(5) Magnetic metal oxide cross-linked acidic polyionic liquid: the magnetic metal oxide cross-linked polyionic liquid was dispersed in deionized water, concentrated sulfuric acid was dropwisely added under an ice bath condition, and the mixture was stirred at room temperature in a water bath, filtered, washed with water, and dried to obtain the magnetic metal oxide cross-linked acidic polyionic liquid.

The metal oxide support in step (2) may be γ-$Al_2O_3$, $ZrO_2$, $TiO_2$, $SnO_2$, or the like, and the obtained magnetic metal oxide cross-linked acidic polyionic liquid was respectively $Fe_3O_4@Al_2O_3$-SH-IM-$HSO_4$, $Fe_3O_4@ZrO_2$-SH-IM-$HSO_4$, $Fe_3O_4@TiO_2$-SH-IM-$HSO_4$ or $Fe_3O_4@SnO_2$-SH-IM-$HSO_4$.

Example 13: Comparison of Catalytic Properties of Magnetic Metal Oxide Cross-Linked Acidic Polyionic Liquid Prepared by Different Metal Oxide Supports The catalytic properties of the magnetic metal oxide cross-linked acidic polyionic liquid prepared by different metal oxide supports were compared as follows:

(1) 50 mg of magnetic metal oxide cross-linked acidic polyionic liquid was respectively weighed and added into a reactor containing 3 mL of DMSO;

(2) 100 mg of xylose was weighed in the reaction system of step (1), and stirred in an oil bath at 140° C. for 3 h, and the reaction product was taken out and cooled after the reaction was finished; and (3) after the reaction product was cooled, 50 µL of sample was taken and diluted to 5 mL with deionized water, and the yield of furfural was determined by a high-performance liquid chromatograph.

After the determination, the results are shown in Table 1.

TABLE 1

Catalytic properties of different magnetic metal oxide cross-linked acidic polyionic liquids.

| Catalyst | Conversion Rate of Xylose | Yield of Furfural | Yield of Furfural After Recycling 5 Times |
|---|---|---|---|
| $Fe_3O_4@Al_2O_3$-SH-IM-$HSO_4$ | 97% | 72% | 63% |
| $Fe_3O_4@ZrO_2$-SH-IM-$HSO_4$ | 85% | 56% | 45% |

TABLE 1-continued

Catalytic properties of different magnetic metal oxide cross-linked acidic polyionic liquids.

| Catalyst | Conversion Rate of Xylose | Yield of Furfural | Yield of Furfural After Recycling 5 Times |
|---|---|---|---|
| $Fe_3O_4$@$TiO_2$-SH-IM-$HSO_4$ | 78% | 47% | 35% |
| $Fe_3O_4$@$SnO_2$-SH-IM-$HSO_4$ | 91% | 58% | 48% |

Example 14: Production of Furfural from Xylose Using Magnetic Metal Oxide Cross-Linked Acidic Polyionic Liquid as Catalyst Similar to the method of Example 6, $\gamma$-$Al_2O_3$ was selected as the oxide support, and the concentrated sulfuric acid in step (5) was replaced with concentrated hydrochloric acid, concentrated nitric acid or concentrated phosphoric acid to obtain the magnetic metal oxide cross-linked acidic polyionic liquid $Fe_3O_4$@$Al_2O_3$-SH-IM-Cl, $Fe_3O_4$@$Al_2O_3$-SH-IM-$NO_3$ or $Fe_3O_4$@$Al_2O_3$-SH-IM-$H_2PO_3$. The properties of the products obtained with different concentrated acids were compared. The method was as follows:

(1) 50 mg of magnetic metal oxide cross-linked acidic polyionic liquid ($Fe_3O_4$@$Al_2O_3$-SH-IM-Cl, $Fe_3O_4$@$Al_2O_3$-SH-IM-$NO_3$, $Fe_3O_4$@$Al_2O_3$-SH-IM-$H_2PO_3$ or $Fe_3O_4$@$Al_2O_3$-SH-IM-$HSO_4$) was weighed and added to a reactor containing 3 mL of DMSO;

(2) 100 mg of xylose was weighed in the reaction system of step (1), and stirred in an oil bath at 140° C. for 3 h, and the reaction product was taken out and cooled after the reaction was finished; and (3) after the reaction product was cooled, 50 μL of sample was taken and diluted to 5 mL with deionized water, and the yield of furfural was determined by a high-performance liquid chromatograph.

It was determined that under the catalytic action of the $Fe_3O_4$@$Al_2O_3$-SH-IM-Cl, $Fe_3O_4$@$Al_2O_3$-SH-IM-$NO_3$, $Fe_3O_4$@$Al_2O_3$-SH-IM-$H_2PO_3$ and $Fe_3O_4$@$Al_2O_3$-SH-IM-F—$HSO_4$, the yield of furfural was respectively 42%, 43%, 55% and 72%.

The above-mentioned examples are better examples of the present disclosure, but are not restrictions on the examples of the present disclosure. In this field, any other changes, modifications, combinations, substitutions and simplifications that do not depart from the principles and spirit of the present disclosure belong to the equivalent replacement mode and are included in the scope of protection of the claims of the present disclosure.

What is claimed is:

1. A magnetic metal oxide cross-linked acidic polyionic liquid prepared by a process comprising the following steps:
   thiolating a metal oxide support, wherein the metal oxide support is $\gamma$-$Al_2O_3$, $ZrO_2$, $TiO_2$ or $SnO_2$,
   crosslinking the metal oxide support with divinylimidazole halide under action of an initiator to obtain a metal oxide cross-linked polyionic liquid,
   wrapping the metal oxide cross-linked polyionic liquid with magnetic nanoparticles to obtain a magnetic metal oxide cross-linked polyionic liquid, and
   reacting the magnetic metal oxide cross-linked polyionic liquid with concentrated acid to obtain the magnetic metal oxide cross-linked acidic polyionic liquid.

2. The magnetic metal oxide cross-linked acidic polyionic liquid according to claim 1, wherein the metal oxide is $Fe_3O_4$@$Al_2O_3$-SH-IM-Cl, $Fe_3O_4$@$Al_2O_3$-SH-IM-$NO_3$, $Fe_3O_4$@$Al_2O_3$-SH-IM-$H_2PO_3$, or $Fe_3O_4$@$Al_2O_3$-SH-IM-$HSO_4$ wherein IM is divinlyimidazolium cation.

3. The magnetic metal oxide cross-linked acidic polyionic liquid according to claim 1, wherein the thiolation of the metal oxide support comprises: adding the metal oxide support with $\gamma$-mercaptopropyltrimethoxysilane in an organic solvent, reacting in an oil bath under an inert gas, cooling, filtering, washing and drying to obtain a thiolated metal oxide support.

4. The magnetic metal oxide cross-linked acidic polyionic liquid according to claim 1, wherein obtaining the metal oxide cross-linked polyionic liquid comprises: under action of the initiator, reacting the thiolated metal oxide support and the divinylimidazole halide in a methanol solvent in an oil bath under an inert condition, cooling to room temperature, filtering, washing with alcohol, and drying to obtain the metal oxide cross-linked polyionic liquid.

5. The magnetic metal oxide cross-linked acidic polyionic liquid according to claim 1, wherein the concentrated acid is concentrated hydrochloric acid, concentrated nitric acid, concentrated phosphoric acid or concentrated sulfuric acid.

6. The magnetic metal oxide cross-linked acidic polyionic liquid according to claim 1, wherein wrapping the metal oxide cross-linked polyionic liquid comprises: dispersing the nanoparticles and the metal oxide cross-linked polyionic liquid in ethanol, stirring vigorously in a water bath, cooling to room temperature, carrying out magnetic separation, washing with alcohol, and drying to obtain the magnetic metal oxide cross-linked polyionic liquid.

7. The magnetic metal oxide cross-linked acidic polyionic liquid according to claim 1, wherein obtaining the magnetic metal oxide cross-linked acidic polyionic liquid specifically comprises the following steps: dispersing the magnetic metal oxide cross-linked polyionic liquid in deionized water, dropwisely adding concentrated acid under an ice bath condition, stirring at room temperature in a water bath, filtering, washing with water, and drying to obtain the magnetic metal oxide cross-linked acidic polyionic liquid.

8. The magnetic metal oxide cross-linked acidic polyionic liquid according to claim 1, wherein the process specifically comprises:
   (1) synthesizing divinylimidazole halide;
   (2) thiolation of the metal oxide support: reacting the metal oxide support with $\gamma$-mercaptopropyltrimethoxysilane in a toluene solvent in an oil bath under an inert condition, cooling to room temperature, filtering, washing with alcohol, and drying to obtain the thiolated metal oxide support;
   (3) under the action of the initiator, reacting the thiolated metal oxide support and the divinylimidazole halide in a methanol solvent in an oil bath under an inert condition, cooling to room temperature, filtering, washing with alcohol, and drying to obtain the metal oxide cross-linked polyionic liquid;
   (4) wrapping $Fe_3O_4$ nanoparticles with metal oxide cross-linked polyionic liquid: dispersing the $Fe_3O_4$ and the metal oxide cross-linked polyionic liquid in ethanol, stirring vigorously in a water bath, cooling to room temperature, carrying out magnetic separation, washing with alcohol, and drying to obtain the magnetic metal oxide cross-linked polyionic liquid; and
   (5) obtaining the magnetic metal oxide cross-linked acidic polyionic liquid: dispersing the magnetic metal oxide cross-linked polyionic liquid in deionized water, dropwisely adding concentrated acid under an ice bath condition, stirring at room temperature in a water bath, filtering, washing with water, and drying to obtain the magnetic metal oxide cross-linked acidic polyionic liquid.

9. A method, comprising adding the magnetic metal oxide cross-linked acidic polyionic liquid of claim 1 as a catalyst to a reaction comprising xylose, catalyzing production of furfural from xylose and obtaining furfural from the reaction wherein the metal oxide support is $\gamma\text{-}Al_2O_3$, $TiO_2$ or $SnO_2$.

10. The method according to claim 9, wherein the xylose and the magnetic metal oxide cross-linked acidic polyionic liquid catalyst are placed into a reactor with the mass ratio of 1:(0.3-0.7), and a reaction solvent is added to react.

11. The method according to claim 10, wherein the reaction solvent is any one or a combination of two or more of DMSO, DMF, DMA, NMP, THF, 2-MTHF, toluene and n-butanol.

12. The method according to claim 11, wherein the addition ratio of the xylose to the reaction solvent is 100 mg: (1-5 mL).

13. The method according to claim 9, wherein the reaction is carried out at 120° C.–160° C. for 1-5 h.

14. The method according to claim 13, wherein the reaction is carried out in an oil bath.

15. The method according to claim 9, wherein the method specifically comprises:
(1) placing xylose and a magnetic metal oxide cross-linked acidic polyionic liquid catalyst in a reactor with the mass ratio of 1:(0.3-0.7), adding a reaction solvent, reacting at 120° C.–160° C. in an oil bath for 1-5 h, and cooling after the reaction is finished;
(2) after the reaction solution in step (1) is cooled, diluting a certain amount of reaction solution with deionized water to a specified volume, and determining conversion rate of xylose and yield of furfural by a high-performance liquid chromatograph; and
(3) after the reaction in step (1) is finished, separating out the catalyst by action of an external magnetic field, washing with alcohol, and drying the catalyst to be re-added to the reaction system of step (1).

16. A preparation method of the magnetic metal oxide cross-linked acidic polyionic liquid of claim 1, comprising: after thiolation of a metal oxide support, crosslinking with divinylimidazole halide under action of an initiator to obtain a metal oxide cross-linked polyionic liquid, then wrapping magnetic nanoparticles with the metal oxide cross-linked polyionic liquid to obtain a magnetic metal oxide cross-linked polyionic liquid, and reacting the magnetic oxide cross-linked polyionic liquid with concentrated acid to obtain the magnetic metal oxide cross-linked acidic polyionic liquid wherein the metal oxide support is $\gamma\text{-}Al_2O_3$, $TiO_2$ or $SnO_2$.

17. The magnetic metal oxide cross-linked acidic polyionic liquid according to claim 1, wherein the metal oxide cross-linked acidic polyionic liquid is $Fe_3O_4@Al_2O_3$-SH-IM-$HSO_4$ wherein IM is divinlyimidazolium cation.

* * * * *